US00PP12224P2

(12) United States Plant Patent
DeJong et al.

(10) Patent No.: US PP12,224 P2
(45) Date of Patent: Nov. 27, 2001

(54) PRUNE TREE NAMED 'TULARE GIANT'

(75) Inventors: Theodore M. DeJong, Davis; James F. Doyle, Clovis, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/493,611

(22) Filed: Jan. 28, 2000

(51) Int. Cl.[7] ..... A01H 5/00

(52) U.S. Cl. ..... Plt./185

(58) Field of Search ..... Plt./185, 184

(56) References Cited

PUBLICATIONS

UPOV–ROM GTITM Computer Database, 2000/06, GTI Jouve Retrieval Software, citation for 'Tulare Giant'.*

* cited by examiner

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct cultivar of prune tree (i.e., *Prunus domestica*) is provided that resulted from a controlled breeding program. The new cultivar exhibits extreme precocity and a vigorous growth habit. Flowers are formed in abundance. Very large early-maturing fruit also is formed in abundance on a regular basis that is dark purple under a greyish and waxy epidermal bloom. The fruit is particularly well suited for the fresh prune market.

1 Drawing Sheet

BACKGROUND OF THE INVENTION

The new cultivar of *Prunus domestica* of the present invention was created during 1987 in the course of prune breeding research carried out at the Kearney Agricultural Center of the University of California located at Parlier, Calif. *Prunus domestica* is commonly known as the European plum. The female parent (i.e., seed plant) was the European plum cultivar 'Empress' (non-patented in the United States) and the male parent (i.e., pollen parent) was the prune cultivar 'Primacotes' (non-patented in the United States). The parentage of the new cultivar is expressed as follows:

'Empress' ×'Primacotes'.

During the course of the breeding program over 259 crosses were attempted following emasculation. Such cross-pollination made possible the harvest of 70 seeds at the end of the growing season. These were planted during 1988 and were given the group designation P88.16. The seedlings were grown in a nursery at Parlier, Calif. and were carefully studied during the remainder of 1988 and 1989. In the spring of 1990 these young nursery trees were transplanted into seedling rows. A single tree of the new cultivar of the present invention was selected during 1991 when such seedling fruited. This seedling initially was designated 3-6E-13.

It was found that the new *Prunus domestica* cultivar of the present invention:

(a) Exhibits a vigorous growth habit, (b) Demonstrates extreme precocity, (c) Forms flowers in abundance, and (d) Forms in abundance very large early maturing fruit that is dark purple under a greyish and waxy epidermal bloom that is particularly well suited for the fresh prune market.

The new cultivar has been asexually reproduced by grafting and budding. During the spring of 1992 the new cultivar was first asexually propagated at Parlier, Calif. by grafting onto two large six year old trees of 'Marianna 2624' plum rootstock (non-patented in the United States). Subsequently the new cultivar additionally has been propagated on the same plum rootstock. 'Myrobalan 29C' plum rootstock (non-patented in the United States), and 'Nemaguard' peach rootstock (non-patented in the United States). The 'Myrobalan 29C' rootstock is botanically classified as *Prunus cerasifera* and is a common rootstock used for prune trees in California. The new cultivar was found to reproduce true to form via such asexual propagation. All propagated trees were found to be very precocious with a small amount of fruit being produced as early as 1993 with a more substantial crop in 1994 and thereafter. Fruit is formed from buds on one-year old wood as well as an older spurs. The new cultivar was found to perform well on both plum rootstocks. On the 'Nemaguard' peach rootstock a substantial outgrowth was found to occur at the graft union and the trees were distinctly smaller in size than when grown on the plum rootstock. Although no breakage has been observed at the union with the peach rootstock, propagation of the new cultivar on peach rootstock is not recommended. Since almost no topstock cultivars of Prunus are grown on their own roots in California, and many superior rootstocks are available, no effort has been made to grow the new cultivar of the present invention on its own roots.

The new cultivar has been further evaluated at test sites in the San Joaquin and Sacramento Valleys of California. These tests have further confirmed the commercial potential of the new cultivar.

In a typical year the fruit of new cultivar commonly reaches maturity during July at Parlier, Calif. This is nearly one month earlier at such location than that produced on the most commonly grown 'Improved French' prune cultivar (non-patented in the United States). The generally oval-shaped fruit is considerably larger than that of the 'Improved French' cultivar. Also, the fruit of the 'Improved French' cultivar tends to be obovate often with a distinct neck and is of a lighter shade of purple than that of the new cultivar. In view of the abundant fruit set commonly achieved on the new cultivar it is recommended that the fruit be thinned on the tree to further enhance the quality of the fruit crop.

The new cultivar of the present invention is particularly well-suited for yielding an attractive and distinctive fresh market prune crop. Currently the fresh prune crop produced in the United States is largely exported to Pacific rim countries where it is held in particularly high regard. At the present time the 'Moyer' cultivar (non-patented in the United States) is believed to be the most commonly grown and sold cultivar for the fresh market. The new cultivar can be readily distinguished from the 'Moyer' cultivar by its larger fruit size and earlier fruit maturity.

Alternatively, the large fruit of the new cultivar can be dried. However, there are some disadvantages when the fruit is dried. The pit is large and is only semi-free from the flesh. Adequate drying times commonly exceed twenty hours and the fruit displays some tendency during drying to bleed, slab, and stick to the drying trays. The quality of the dried flesh is good, but because of such observations, utilization as a dried produce is less preferred.

The new cultivar of the present invention readily can be distinguished from its 'Empress' plum parent in view of differences with respect to time of ripening, tree form, fruit soluble solids, and sensitivity to heat. The new cultivar commonly ripens in early July in the San Joaquin Valley of California, and the 'Empress' cultivar commonly ripens in late August at the same location. The trees of the 'Empress' cultivar tend to be very open and not highly branched. On the contrary, the new cultivar displays a well-branched tree that is capable of bearing heavy crops. The soluble solids level of the 'Empress' cultivar commonly ranges from 12 to 15 degrees Brix at full maturity. This can be compared to 17 to 22 degrees Brix for the new cultivar at soft ripe maturity. The 'Empress' cultivar is not grown commercially in the San Joaquin Valley of California because of its high sensitivity to fruit internal heat damage. On the contrary, the new cultivar can be grown to advantage in the hot interior California valleys.

The new cultivar of the present invention readily can be distinguished from its 'Primacotes' prune parent in view of substantial differences with respect to fruit shape, fruit color, distribution on the tree, productivity, and sensitivity to heat. The fruit of the 'Primacotes' cultivar is pyridiform-shaped with a broad but distinct neck and is reddish to reddish-purple in color when ripe. The fruit of the new cultivar is oval and possesses no neck, and when ripe is dark purple under a grey bloom. The fruit of the 'Primacotes' cultivar is borne in large clusters on the end of the previous season's shoots with very little fruit being present on older shoots or spurs. On the contrary, the fruit of the new cultivar is borne throughout the tree both on the previous season's shoots as well as on the older hanger shoots and spurs. This leads to greater productivity for the new cultivar. The 'Primacotes' cultivar when grown in the hot interior San Joaquin Valley of California, can show a moderate amount of fruit internal heat damage. On the contrary, the new cultivar at the same location is highly adapted and has never exhibited heat damage.

The new cultivar has been named 'Tulare Giant'.

BRIEF DESCRIPTION OF THE PHOTOGRAPH

The accompanying photograph shows typical specimens of the foliage, fruit (with and without the epidermal bloom), fruit flesh, and pit of the new cultivar as depicted in color as nearly true as it is possible to make the same in a color illustration of this character. The tree of the new cultivar was grown at the Kearney Agricultural Center of the University of California at Parlier, Calif. The fruit shown in the photograph was harvested during July and was at near full commercial maturity.

DETAILED DESCRIPTION

The following is a detailed description of the new prune tree cultivar that was obtained from the observation of eight year-old asexually propagated trees during the 1999 growing season (except where otherwise indicated). The trees were propagated on *Prunus cerasifera* 'Myrobalan 29C' plum rootstock. The trees were grown at the Kearney Agricultural Center of the University of California located at Parlier, Calif. Tree spacing was 5.49 m between rows and 4.88 m spacing between trees down the row. The color chart used in the identification of colors is that of The Royal Horticultural Society, London (R.H.S. Colour Chart). Other color terminology is to be accorded its customary dictionary significance.

Botanical classification: *Prunus domestica*, cv. 'Tulare Giant'.

*Female parent.*—cv. 'Empress'.

*Male parent.*—cv. 'Primacotes'.

Tree:

*Size.*—The height during October at the end of the growing season ranges from approximately 4.2 to 4.7 m including approximately 1.7 to 1.8 m of current season's growth. The width across the crown ranges from approximately 3.7 to 4.3 m.

*Vigor.*—Good.

*Growth.*—Upright-spreading to spreading.

*Hardiness.*—Hardy under typical San Joaquin Valley of California climatic conditions.

*Production.*—High fruit productivity.

*Bearing.*—Regular bearer.

Trunk:

*Size.*—Average in thickness for *Prunus domestica*. The trunk circumference at 35 cm above the ground is approximately 12 cm.

*Texture.*—Relatively smooth with only a slight amount of short scarfskin.

*Color.*—Greyed-Green Group 197A to Brown Group 200B.

*Lenticels.*—Numerous, prominent, oval in configuration, most pronounced on the trunk and large scaffold limbs where they are the most abundant, and commonly raised with a calloused surface. The height commonly ranges from approximately 1.5 to 2.0 mm and the width from approximately 2.0 to 6.0 mm. The coloration is brownish-tan, near Grey-Orange Group 173C.

Branches:

*Diameter.*—Average thickness for *Prunus domestica*. The diameters of primary scaffold branches average 7.4 cm and range from 6.1 to 8.4 cm, and the diameters at the base of the secondary scaffold branches average 4.5 cm and range from 3.3 to 5.7 cm. The basal diameters of fruiting hanger limbs average 1.1 cm and range from 0.7 to 1.7 cm. The diameters of fruiting spurs average 0.5 cm with a range from 0.3 to 0.7 cm. These dimensions were obtained from the observation of ten-year-old trees during April 2001.

*Surface.*—Substantially pubescent especially on current season's growth. Such pubescence is moderately dense and short.

*Color.*—Branch color is somewhat variable. Mature current season's shoots are medium brown of near Brown Group 200D. Immature shoots range from light green of Yellow-Green Group 144B to darker green of Yellow-Green Group 144A on more mature growth. Young shoots exposed to the direct sunlight often are blushed with a rose-red hue of Red Group 48A. New expanding shoot tips commonly are bright yellow-green of Yellow-Green Group 151A. Two year-old or older branches commonly are near Grey-Brown Group 199B to darker brown of Grey-Brown Group 199A.

*Lenticels.*—Substantial presence on mature current season's shoots, and two year-old or older branches.

*Internode length.*—Normal for *Prunus domestica*. The distance between nodes commonly ranges from approximately 19 to 36 mm on moderately vigorous current season's shoots.

Leaves:

*Size.*—Medium to large. Leaves produced near mid-shoot on vigorous current season's shoots range in length from approximately 10.9 to 15.4 cm including the petiole and in width from approximately 5.5 to 6.8 cm. The leaves are moderately thick and are slightly above average in thickness.

*Arrangement.*—Spiral as arise from shoots.

*Form.*—Variable, frequently obovate, and with the occasional presence of oval leaves. The leaf apices are acute and commonly are very slightly reflexed sideways. With advancing maturity some older leaves are folded downwards from the midrib.

*Color.*—The upper surface is dark green. Yellow-Green Group 146A to Yellow-Green Group 147A. The under surface is lighter green, Yellow-Green Group 147C to Yellow-Green Group 148C. The primary mid-vein on the under surface is pale green, Yellow-Green Group 145C. Both the under surface and the leaf mid-vein on the under surface are highly pubescent.

*Margin.*—Crenate with large somewhat irregular crenations. The margins tend to be slightly undulate.

*Venation.*—Pinnate pattern.

*Petiole.*—Average in size, commonly approximately 17 to 32 mm in length, approximately 1.5 to 2.0 mm in thickness, and light green, Yellow-Green Group 145B, in coloration. With advancing age the petiole coloration can darken and assume a reddish blush near Red Group 37A. Such blush tends to be most evident along the ridges of the petiole groove.

*Glands.*—From 0 to 2 small glands commonly can be observed at the extreme base of the leaf blade margin. Such glands are globose in configuration and occur on stalks which are distinct or indistinct. Usually no glands are present on the petiole itself. The gland position is alternate. The coloration when young is bright green, Yellow-Green Group 151C, with darkening and deterioration with age.

*Stipules.*—Medium to large in size, linear lanceolate in configuration, located at the very base of the petiole and arise from the base of the petal groove area, partially deciduous with some stipules remaining on the leaf throughout the growing season, margins are serrate and substantially pubescent, commonly approximately 5 to 11 mm in length and 1.5 to 2.0 mm in width at full maturity, and the coloration of young stipules is green, Yellow-Green Group 145A.

Fruit:

*Maturity when described.*—Full ripe.

*Picking.*—First pick was July 30th and the last pick was Aug. 9, 1999. The 1999 fruit growing season in the San Joaquin Valley area of California was one of the latest on record and ranged from 12 to 15 days later than average. A more typical first-pick date is July 15th and a more typical last pick date is July 25th.

*Size.*—Very large for the species and of relatively good uniformity. Fruit from a well-thinned tree ranges from approximately 40 to 53 mm in the suture diameter and approximately 54 to 68 mm in the axial diameter.

*Form.*—Most frequently oval in lateral aspect, is well rounded basally and apically, and tends to be slightly more pointed apically. Nearly globose to slightly oval in the apical aspect and at times is slightly irregular. The fruit varies from symmetrical to slightly asymmetrical.

*Suture.*—Very thin, with a somewhat indistinct line extending from the base to apex. Most frequently is similar in coloration to that of the surrounding skin surface. At times is slightly depressed especially over the ventral apical shoulder. A very slight amount of stitching occasionally is observed over the apical shoulder.

*Ventral surface.*—Usually quite smooth; however, at times a very low lipping is observed.

*Stem cavity.*—Oval, quite regular in configuration, very small, tight and very shallow. The width commonly ranges from approximately 2.5 to 5.0 mm and the depth commonly ranges from 2.0 to 2.5 mm. At times a small oval fleshy ring is observed within the cavity basin which surrounds the stem at the point of attachment to the basal cavity. Such ring is narrow and averages approximately 1.0 mm in thickness. When the stem is removed from the fruit, the ring can remain in the cavity or be attached to the distal end of the stem.

*Base.*—Regular and rounded. The stem attachment and stem cavity frequently are not positioned at the highest point of the fruit base, but rather are positioned approximately 5 to 8 mm down the ventral edge from the basal apex. The basal angle tends to be decidedly oblique to the fruit axis.

*Apex.*—Slightly raised and somewhat more pointed than the fruit base with no depression at the apex. The pistil point is variable and at times is apical and at times is moderately oblique.

*Stem.*—Medium in length and pubescent with the abundant presence of short and stiff hairs. The length commonly ranges from approximately 11 to 18 mm. The thickness commonly ranges from 1.5 to 2.0 mm. The color is pale green at commercial maturity, near Yellow-Green Group 146C.

*Skin pubescence.*—Generally glabrous but with a small amount of scattered very fine pubescence covering the surface of the fruit.

*Skin thickness.*—Relatively thick.

*Skin flavor.*—Slightly acidic.

*Skin tendency to split.*—No tendency to crack or split has been observed.

*Skin tenacity.*—Tightly attached to fruit at commercial maturity.

*Skin color.*—Grey-blue, Violet-Blue Group 97B, at commercial maturity when the waxy cuticle bloom is intact. Once the bloom is removed the coloration is dark purple, Greyed-Purple Group 187A. The fruit usually is fully colored with no visible ground color. Occasionally a lighter reddish-purple, Greyed-Purple Group 187C, is observed especially on an exposed fruit surface. At full maturity a small number of light colored dots sometimes are observed, primarily on the lateral surfaces and over the basal shoulder.

*Flesh color.*—Commonly varies from Yellow-Orange Group 20B to a darker yellow orange, Yellow-Orange Group 20A. A small number of fibers also commonly are observed within the stone cavity and along the margins of the stone.

*Flesh texture.*—At commercial maturity the flesh is firm, relatively fine textured, and moderately juicy. At more advanced maturity the fruit becomes softer and very juicy.

*Ripening.*—Ripens evenly.

*Flavor.*—Mild and sweet with a relatively low acidity. During the 1999 growing season on July 30th, soluble solids reached 17 degrees Brix at 5.0 pounds pressure for fresh shipment. On August 13th of the same year, soluble solids reached 20 degrees Brix at a drying maturity of 2.6 pounds pressure.

*Aroma.*—Very slight to lacking at commercial maturity. The aroma becomes slightly stronger as maturity progresses.

*Eating quality.*—Good.

*Processing quality.*—Limited as a dried product.

Stone description:

*Attachment.*—Semi-freestone. The flesh fibers are attached primarly at the base of the stone and along the suture edges, but are generally free laterally. The stone tends to become more free with advancing maturity.

*Size.*—Relatively large, commonly ranges from approximately 28 to 33 mm in length, approximately 14 to 17 mm in width, and approximately 7.5 to 9.5 mm in thickness.

*Form.*—Normal oval.

*Base.*—Distinctly oblique to the axis.

*Hilum.*—Very small and commonly averages approximately 2 to 3 mm in length. Is oval, but the shoulder commonly is distinctly eroded along the ventral edge. The basal area under the hilum scar is somewhat necked. Distinct ridges commonly are present on the basal neck which converge basally.

*Apex.*—Acute in form.

*Sides.*—Variable and range from nearly equal to distinctly unequal.

*Surface.*—Slightly rough with the lateral surfaces being covered with very low netted ridges.

*Ventral edge.*—Relatively narrow, smooth and regular. Very low wings of often less than 1 mm sometimes are present on the basal one-third of the ventral edge and sometimes are completely absent. Commonly a shallow but distinct groove is present laterally and runs roughly parallel to the ventral edge at approximately 2 to 3 mm below the edge. The ventral edge sometimes is slightly pitted and at times is discontinuous.

*Dorsal edge.*—A distinct groove commonly is present along the dorsal edge from the base to the apex. At times the dorsal groove is discontinuous at or near med-suture. The dorsal groove is usually wider and more distinct from the base of the stone up to mid-suture. The groove tends to be narrower beyond mid-suture towards the apex.

*Color.*—Cinnamon, Greyed-Orange Group 165C. The wet color is darker, Greyed-Orange Group 165B.

*Tendency to split.*—None observed.

*Chilling season.*—Data for this description was obtained during March 1999. There were approximately 1331 chilling hours below 45° F. for the 1998–1999 winter season.

*Floral buds.*—Medium in size, commonly 4 to 5 mm in length and 2 to 3 mm in width, conic in form, plump, slightly appressed to the bearing stem, and hardy under typical San Joaquin Valley climatic conditions. The bud surface scales are dark brown, Brown Group 200B, in coloration, are lightly pubescent, and are most distinct along the margins. The number of buds per node can range from approximately 1 to 6 and most commonly is approximately 3. Such buds commonly are present in abundance on one year-old wood which is uncommon for the species.

*Blooming time.*—Early in relation to other *Prunus domestica* cultivars. Initial sustained bud burst began on Mar. 14th during 1999. Full bloom occurred on Mar. 19th during 1999. The duration of bloom was approximately 10 days with nearly complete shatter by Mar. 24th in 1999. In contrast the 'Improved French' cultivar attained full bloom on March 28th under the same conditions.

*Size.*—Medium to large for the species. The fully expanded flower diameter commonly is approximately 22 to 30 mm.

*Bloom quantity.*—Abundant.

*Petals.*—Medium to large in size and commonly range from approximately 11 to 14 mm in length and approximately 10 to 12 mm in width. The number is 5 per flower. The form varies from oval to very slightly obovate and at times is notched at the apex. The coloration is white, White Group 155B. The petal claw is short and truncate, approximately 0.5 to 1.0 mm in length and approximately 1.0 mm in width. The margins are variable and range from relatively smooth to slightly undulate and are somewhat cupped inwards. The apices are also somewhat variable and range from smoothly rounded to distinctly notched.

*Pedicel.*—Commonly approximately 7 to 12 mm in length and a thickness of approximately 0.8 to 1.0 mm. The coloration is light green, Green Group 143C, and the surface is pubescent with short erect hairs throughout.

*Nectaries.*—Bright greenish-yellow, Yellow-Green Group 153C, in coloration.

*Calyx.*—Lightly pubescent with short fine pubescence, and greenish-yellow in coloration, Yellow-Green Group 146C.

*Sepals.*—Five in number, approximately 5 mm in length, approximately 3 to 4 mm in width, pubescent on the surfaces with greater density along the margins, oval in form, and the external coloration is light green, Green Group 143C.

*Anthers.*—Average in size, and yellow-gold, Yellow Group 13A, both ventrally and dorsally in coloration.

*Pollen.*—Abundant and yellow-gold, Yellow-Orange Group 14A, in coloration.

*Stamens.*—Approximately 20 to 27 and most frequently approximately 25, the length is variable and commonly approximately 5 to 9 mm, and commonly equal in height to slightly shorter than the pistil. The filament color is white, White Group 155B.

*Pistils.*—The surface of the ovary is pubescent and surface of the style is substantially glabrous. The length including the ovary is approximately 10 to 13 mm. The style is yellow-green, Yellow-Green Group 145C, and the ovary is darker shiny green, Yellow-Green Group 144B, in coloration. Under normal environmental conditions only one pistil is present per flower. In seasons following very hot summers it is possible to observe a low number of double pistils (e.g., 2 to 3 percent).

We claim:

1. A new and distinct cultivar of *Prunus domestica* tree exhibiting the following combination of characteristics:

(a) Exhibits a vigorous growth habit, (b) Demonstrates extreme precocity, (c) Forms flowers in abundance, and (d) Forms in abundance very large early-maturing fruit that is dark purple under a greyish and waxy epidermal bloom that is particularly well suited for the fresh prune market, substantially as herein shown and described.

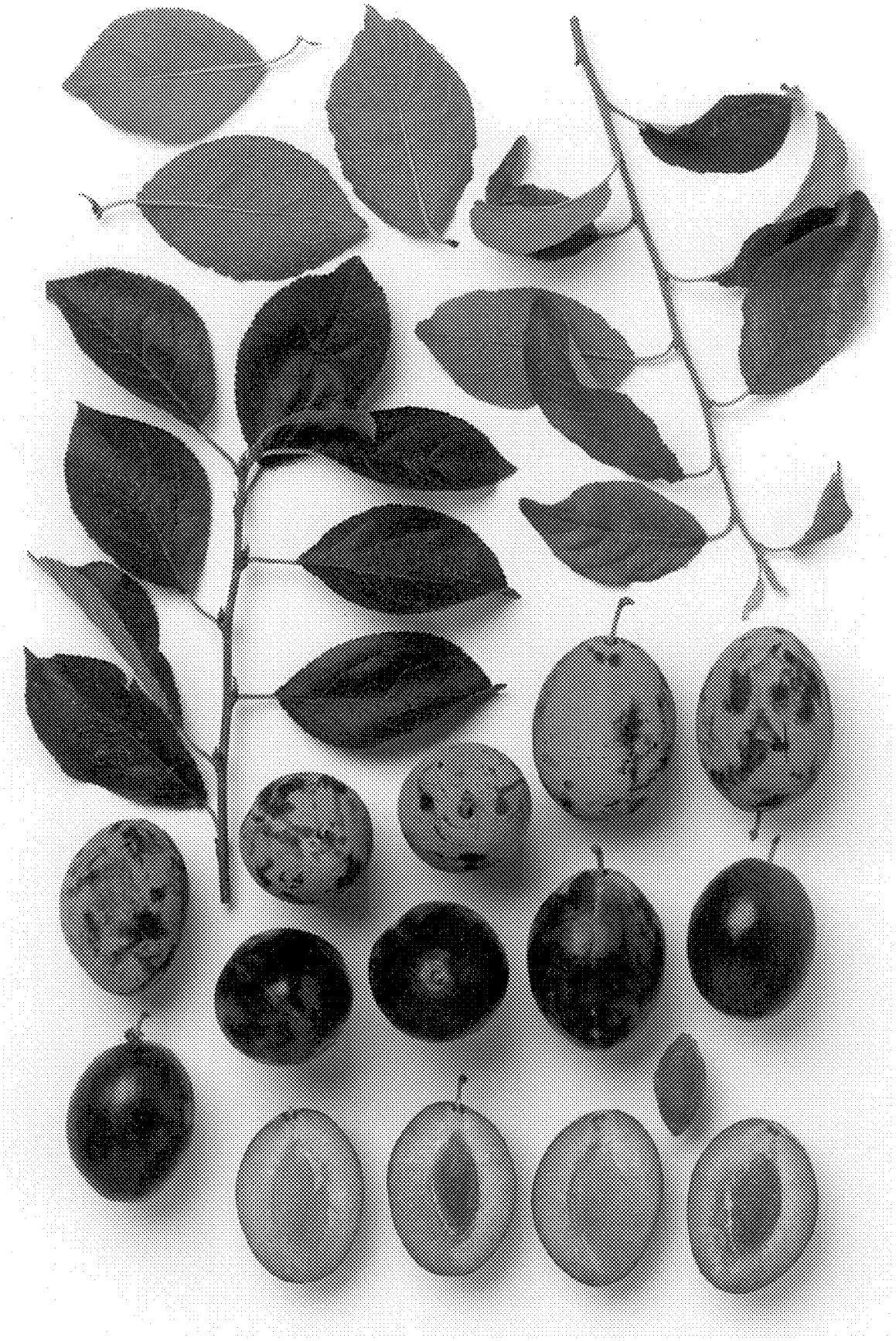

* * * * *